United States Patent
Huynh

(10) Patent No.: US 8,419,431 B2
(45) Date of Patent: Apr. 16, 2013

(54) PREFORMED PROVISIONAL CROWNS AND METHODS FOR CONSTRUCTING TEMPORARY DENTAL CROWNS AND BRIDGES

(76) Inventor: Quang D. Huynh, Garden Grove, CA (US)

(*) Notice: Subject to any disclaimer, the term of this patent is extended or adjusted under 35 U.S.C. 154(b) by 0 days.

(21) Appl. No.: 12/910,627

(22) Filed: Oct. 22, 2010

(65) Prior Publication Data

US 2012/0100506 A1    Apr. 26, 2012

(51) Int. Cl.
  *A61C 13/08*   (2006.01)
  *A61C 13/10*   (2006.01)
(52) U.S. Cl.
  USPC ..................................... 433/202.1; 433/191
(58) Field of Classification Search .......... 433/213–215, 433/32–36, 18–223, 199.1–205, 226; 264/16–20
  See application file for complete search history.

(56) References Cited

U.S. PATENT DOCUMENTS

| | | | |
|---|---|---|---|
| 2,213,964 A * | 9/1940 | Myerson | 433/183 |
| 3,641,670 A | 2/1972 | Karageorge | |
| 3,675,327 A * | 7/1972 | Huget et al. | 433/215 |
| 3,881,251 A | 5/1975 | Valen | |
| 4,380,432 A * | 4/1983 | Orlowski et al. | 433/9 |
| 4,678,435 A | 7/1987 | Long | |
| 4,704,089 A | 11/1987 | Shoher et al. | |
| 4,789,338 A | 12/1988 | Eisenmann | |
| 6,039,569 A | 3/2000 | Prasad et al. | |
| 6,190,171 B1 | 2/2001 | Hajjar et al. | |
| 6,200,136 B1 | 3/2001 | Prasad et al. | |
| 6,250,925 B1 | 6/2001 | Marshall | |
| 6,257,892 B1 | 7/2001 | Worthington | |
| 6,884,073 B2 | 4/2005 | Chilibeck | |
| 7,726,970 B2 | 6/2010 | Worthington | |
| 2001/0036618 A1* | 11/2001 | Worthington | 433/183 |
| 2004/0076925 A1* | 4/2004 | Kim | 433/180 |

* cited by examiner

*Primary Examiner* — Yogesh Patel
(74) *Attorney, Agent, or Firm* — Law Office of Austin Bonderer, PC; Austin Bonderer

(57) ABSTRACT

Apparatuses and methods for providing crowns and bridges is disclosed. The apparatuses include provisional preforms which can have cavities, windows and slits that enable material and linear members to extend through for engagement with adjacent teeth or other preforms. The methods also include ways in which to create crowns and bridges using the preforms.

5 Claims, 6 Drawing Sheets

PREFORMED PROVISIONAL CROWNS AND METHODS FOR CONSTRUCTING TEMPORARY DENTAL CROWNS AND BRIDGES

BACKGROUND OF THE INVENTION

In dentistry, when a tooth is prepared for a permanent crown or a bridge, a provisional crown or bridge is provided while the permanent crown or bridge is manufactured. Currently, there are preformed temporary crowns available. However, these preformed temporary crowns can only be used for the single purpose of making a single unit temporary crown. Thus, there is room for improvement in the art.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION OF THE DRAWINGS

Figure 1A:
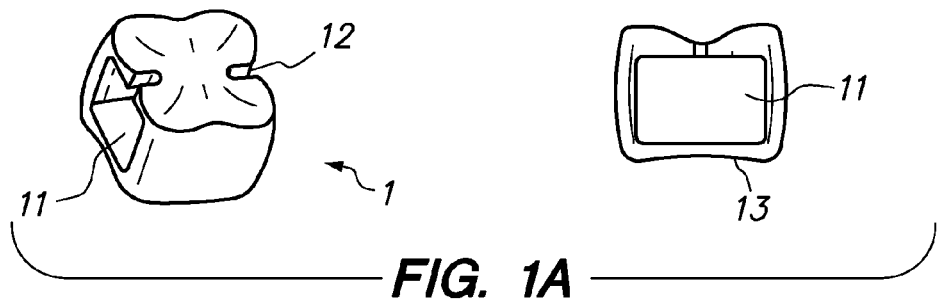
FIGS. 1A-1D show views of several embodiments of preform temporary crowns.
Figure 1B:
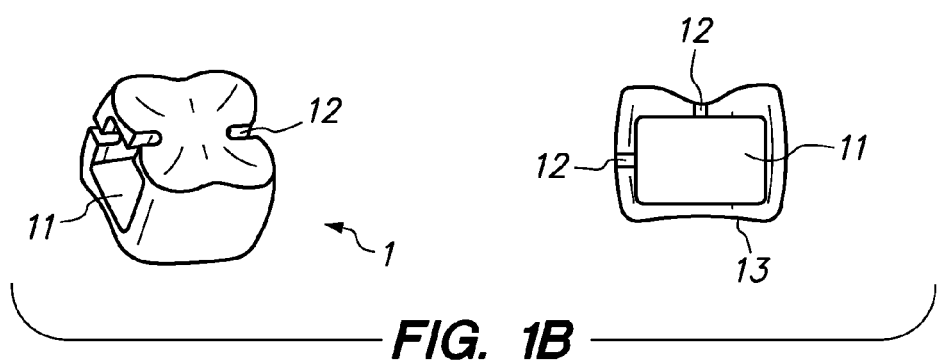
Figure 1C:
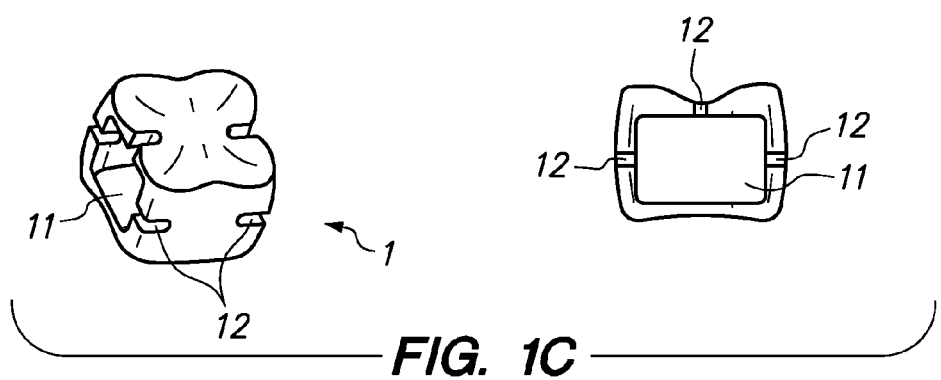

Referring to FIGS. 1A-1D, embodiments of preform temporary crowns (PTCs) are shown. The PTCs are preforms used in the construction of temporary crowns that can be used in the construction of bridges. The PTCs can be made of plastics, including polycarbonate or polymethylmethacrylate, composites, cellulose acetate, metals and/or combinations thereof. The walls of the PTCs can be very thin. In FIGS. 1A-1C, embodiments of posterior preform temporary crown (PPTC) are shown. The PPTC 1 has one or more windows 11. The windows 11 are located on the mesial and/or distal surface of the PPTC 1. Windows 11 located on the mesial surface can be considered mesial windows, and windows 11 located on the distal surface can be considered distal windows. In some embodiments, the windows 11 can comprise a large percentage of the surface area of the side in which they are located (e.g. greater than 50%). The PPTC 1 also has one or more slits 12 that extend from one or more windows 11. The slits 12 can be defined by the occlusal surface, lingual surface, facial surface, mesial surface, distal surface or any combination of surfaces thereof. Slits 12 located on the mesial surface can be considered mesial slits, and slits 12 located on the distal surface can be considered distal slits. The slits 12 can have rectangular cross-sections.

As seen in the embodiment shown in FIG. 1A, there are two slits 12 that extend from the windows 11 and are defined in the mesial and distal surfaces and extend to the occlusal surface. In the embodiment shown in FIG. 1B, an additional slit 12 extends from the window 11 to the lingual surface. The slits 12 can also extend onto the facial surface as seen in the embodiment shown in FIG. 1C.

Figure 1D:
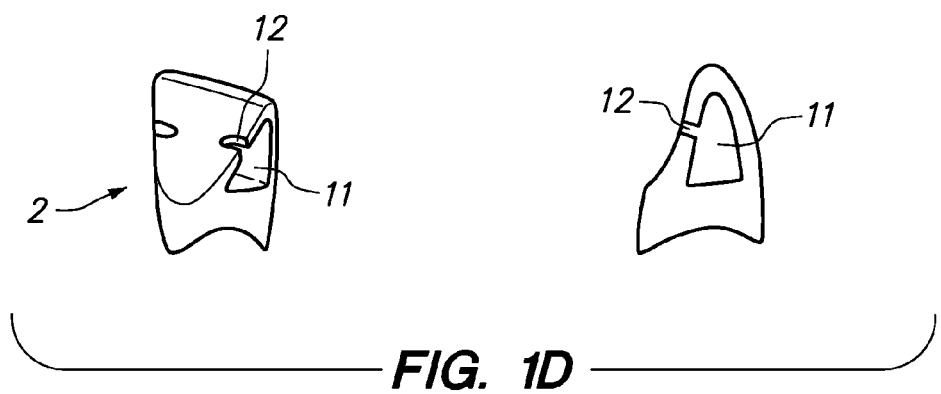

Anterior teeth have a different shape than the posterior teeth due to their purpose, thus the anterior preform temporary crown (APTC) roughly has a triangle-like shape. An embodiment of the APTC 2 is shown in FIG. 1D. The APTC 2 has one or more windows 11, with a triangle like shape, and one or more slits 12. The windows 11 are located on the mesial and/or distal surface of the APTC 2. In some embodiments, the windows 11 can comprise a large percentage of the surface area of the side in which they are located (e.g. over 50%) and/or have other shapes. As shown in FIG. 1D, the slits 12 can extend from the windows 11 to the lingual surface of the APTC 2. It is understood that the one or more slits 12 of an APTC 2 can extend to incisal edge, lingual surface, facial surface, mesial surface, distal surface or any combination of surfaces and edge thereof. It is understood that the PTCs have a top surface, and the top surface will be an incisal edge or an occlusal surface depending on the type of PTC.

Typically when temporary crowns are fitted, the tooth is primed by decreasing the volume of the tooth that is to receive a crown. Material, such as resin that will harden, is added to the cavity of the preforms. Resins include well known acrylic resins, such as methyl methacrylate, ethyl methacrylate, methyl ethyl methacrylate, Bis-GMA, bis-acryl and/or combinations thereof. The preform with the resin is then placed on the tooth and held in place until the resin hardens. Then, the preform is removed, trimmed and polished, and the finished temporary crown is cemented into place with a temporary cement, such as Tempbond. However, this type anchoring sometimes comes lose before the permanent crown is applied.

The windows 11 of the APTCs 2 and the PPTCs 1 are large and allow for the resin to extrude through the windows 11 and come into contact with adjacent teeth. The resin will form a connection with the primed tooth 6 and/or adjacent teeth via the windows 11. It is to be understood that the resin can also extrude through the slits 12. After the resin has hardened, the dentist will remove any excess resin and may remove the PPTC 1 or the APTC 2. In some embodiments, the PTCs are comprise polymer materials, such as methyl methacrylate and polymethylmethacrylate. These polymer materials are very similar to acrylic resin, and when used together, the form a chemical bond to each other. Due to this bond, the PTCs are not removed. The connection between the crown and the adjacent teeth help prevent the lodging of material between the crown and the adjacent teeth.

Figure 2A:
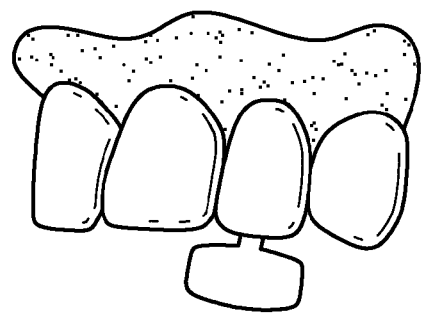
FIGS. 2A-2D show an embodiment of a method of constructing a provisional crown.
Figure 2B:
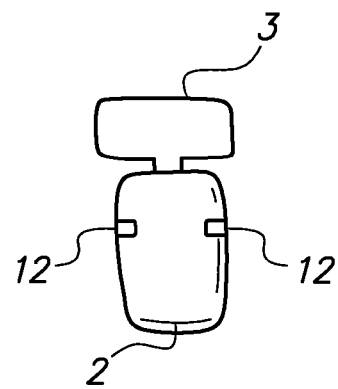
Figure 2C:
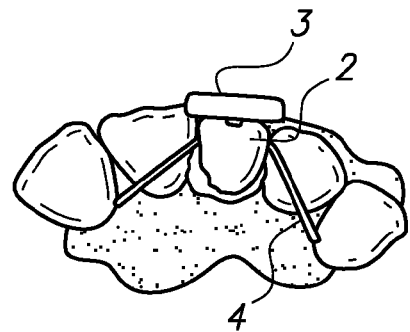
Figure 2D:
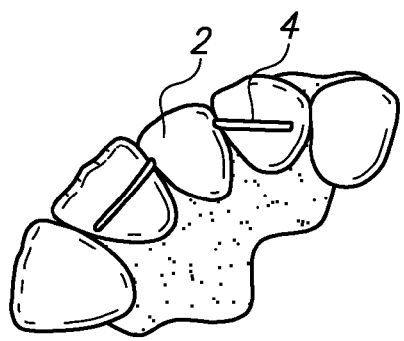

As seen in FIGS. 2A-2D, an embodiment of a method for applying an embodiment of a temporary crown is shown. An APTC 2 is selected. In the embodiment shown in FIG. 2B, the APTC 2 has two slits 12, mesial and distal, defined in the lingual surface. A linear member 4 is inserted through the windows 11 and placed in the slits 12. The APTC 2 is then filed with resin and placed on the tooth as seen in FIG. 2C. Some of the resin will extrude through the windows 11 and maybe out the bottom 13. In some embodiments, the resin is a composite resin that can be hardened when exposed to the ultra violet light. After the resin has hardened, any excess resin on APTC 2 is trimmed and polished. The linear member 4 can be pressed so that it abuts or is near the lingual surface of one or more adjacent teeth. An adhesive is used to adhere the linear member 4 and/or the mesial and distal surfaces of APTC 2 to the adjacent teeth. In some embodiments the adhesive is a composite that will harden in response to exposure to ultraviolet light. It is to be understood that a PPTC 1 can be used in the same manner.

Figure 3A:
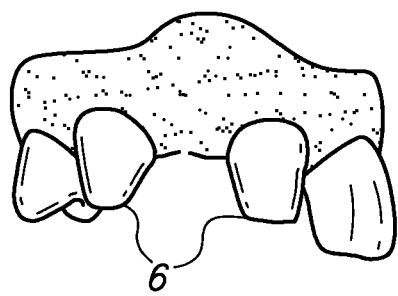
FIGS. 3A-3I show an embodiment of a method of constructing a provisional bridge.
Figure 3B:
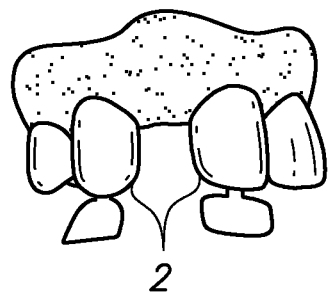
Figure 3C:
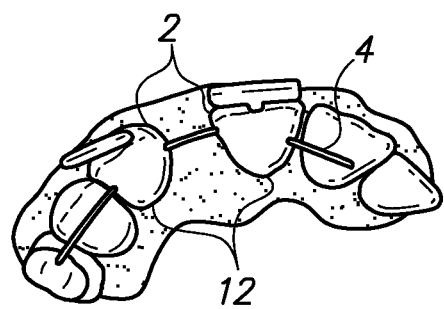
Figure 3D:
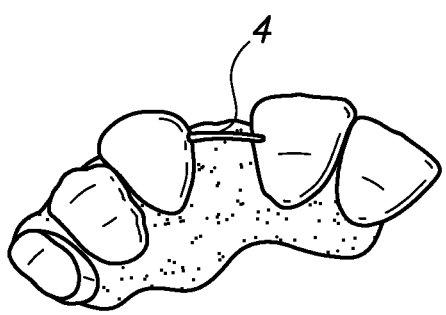
Figure 3E:
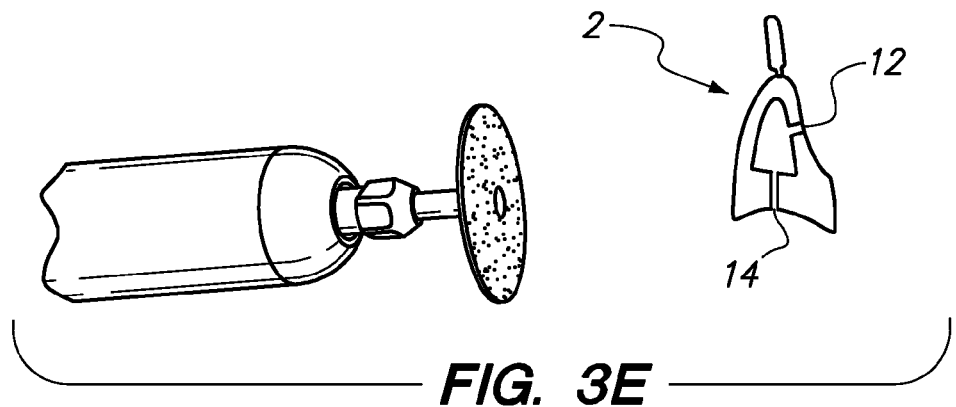
Figure 3F:
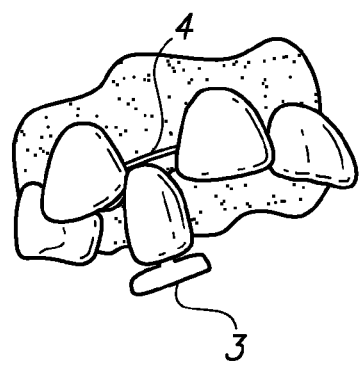
Figure 3G:
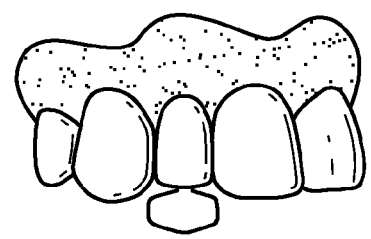
Figure 3H:
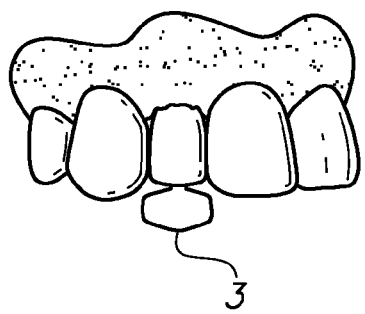
Figure 3I:
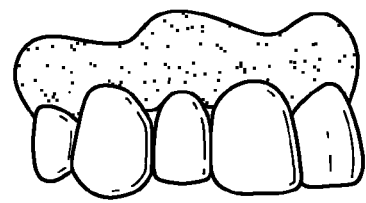

The PPTC 1 and the APTC 2 can also be used to create a three unit bridge. Referring to FIGS. 3A-3I, an embodiment of a method of creating an embodiment of a bridge is shown. The two adjacent teeth are primed by reducing the volume thereof. Three APTCs 2 are selected to fit on the adjacent teeth and fill the gap. Two of the APTCs 2 serve as abutment crowns and one serves as a pontic crown. It is understood that one or more pontic crowns can be used. A linear member 4 is run though the windows 11 and the slits 12. In one embodiment, as seen in FIG. 3C, the linear member 4 is situated in the adjacent windows 11 of the two APTCs 2 and spans across the expanse of the gap. Additionally, the ends of the linear member 4 protrude from slits 12 defined on the lingual surface of the APTCs 2. The two abutments APTCs 2, with the linear member 4 therein, are filled with a resin and placed on the primed teeth 6. After the resin has hardened, the excess linear member 4 and resin and are removed if needed. A single APTC 2 is selected to fill the gap and serve as the pontic crown. The pontic APTC 2 is cut by the user with an implement (e.g. a rotary saw) to establish the slots 14 that extend from the bottom 13 to the windows 11. The cavity is filled with resin, and the slots 14 are slid over the linear member 4 into place to fill the gap. In some embodiments, the resin will extrude out the windows 11 and make contact with the abutment crowns. After the resin has hardened in the pontic APTC 2, the bridge is removed, any excess resin is removed and/or polish, and the temporary bridge is then cemented into place. In other embodiments, the slots 14 can be defined during the manufacturing process. In some embodiments, there can be a perforation that will enable the use to pull the perforation apart by hand to establish the slots 14 when the slots 14 are required. In other embodiments a slot indicator can be present on the PTC. It is understood that the perforation can serve as a slot indicator. As can been seen in the figures, the PTCs may also have a removable tab 3 that aids in the handling of the PTCs.

Figure 4A:
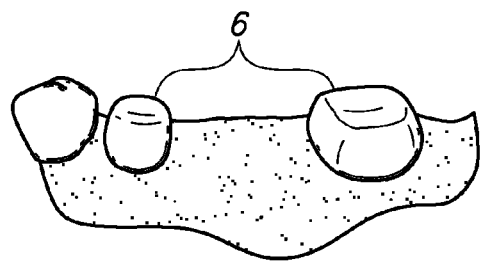
FIGS. 4A-4D show an embodiment of a method of constructing an embodiment of a provisional bridge.
Figure 4B:
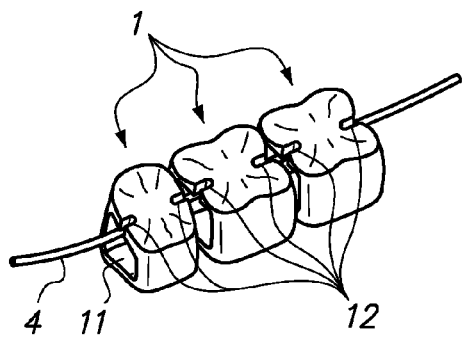
Figure 4D:
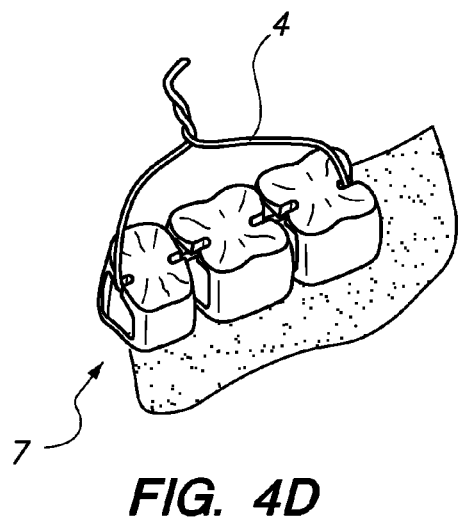
Figure 4C:
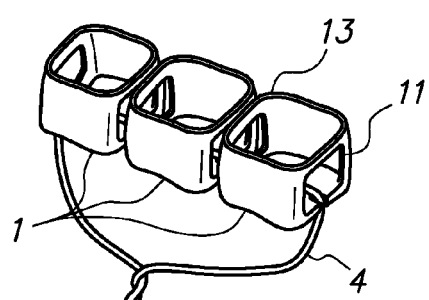

Referring to FIGS. 4A-4D, an embodiment of a method to make an embodiment of a bridge is shown. The adjacent teeth to the gap are primed, and suitable PPTCs 1 are selected. In the embodiment shown in FIGS. 4A-4D, the PPTCs 1 serve as two abutment crowns and one pontic crown. It is understood that one or more pontic crowns can be used. As can been seen in FIG. 4B, a linear member 4 is run though the windows 11 of the PPTCs 1. The PPTCs 1 are then placed over the primed teeth 6 and the gap. The ends of linear member 4 maneuvered in such that the PPTCs 1 are pressed together and form a single unit 7 from the PPTCs 1. The end portions of the linear member 4 can be twisted together, folded over the occlusal surface, folded over the lingual surface, folded over the facial surface, or any combination thereof. The forming of the unit 7 can be done in situ or outside the patient's oral cavity. As can be seen in FIGS. 4C and 4D, the linear member 4 is situated in the slits 12 located on the occlusal surface of the outer most PPCTs 1. The slits 12 in the occlusal surface (or other surfaces) allow the linear member 4 better secure the outermost PPCTs 1 when forming the unit 7. After the unit 7 is formed, it is filled with resin, place in the desired location, and allowed to harden. Then the PPCTs 1 are removed, the linear member 4 cut, and excess resin and/or linear member 4 is removed (e.g. ground down) if need be. The bridge is then formed. Given the windows 11, the resin is able to make a unitary structure even though there are three individual PPCTs 1 in the unit 7. Additionally, the linear member 4 that extends though the entire unitary structure will reinforce the unit 7. In other embodiments, two or more preforms are used to make the unit 7. In one embodiment, one APCT 2 and three PPCTs 1 are used to form the unit 7. It is also understood that a plurality of linear members 4 can be used and extend over the occlusal surface, the lingual surface, the facial surface, or any combination thereof (e.g. one linear member 4 can be folded over the occlusal surface and another linear member 4 can be folded over the lingual surface).

Figure 5A:
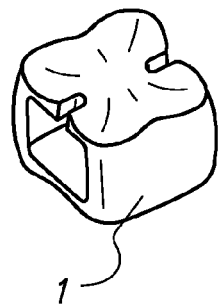
FIGS. 5A-5E show an embodiment of a method of constructing an embodiment of provisional bridge.
Figure 5B:
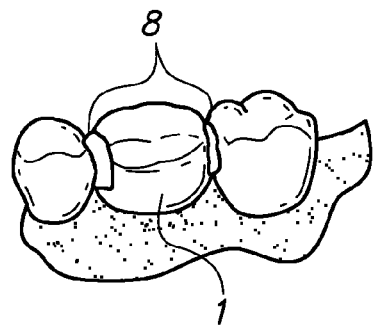
Figure 5D:
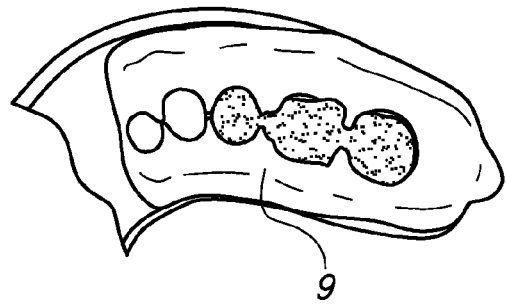
Figure 5C:
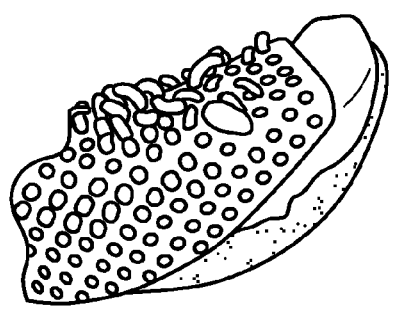
Figure 5E:
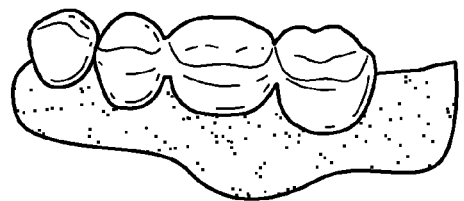

Referring to FIGS. 5A-5E, an embodiment of a method for making an embodiment of a bridge is shown. A PPCT 1 is filled with a material that is malleable at room temperature, such that the malleable material 8 is extruded from both the mesial and distal windows 11. Examples of malleable material are wax, poly-vinyl siloxane and silicone impression material, poly-vinyl siloxane and silicone putty, acrylic, and alginate material. The malleable material 8 will form a connection between the PPCT 1 and the adjacent teeth. An impression 9 is then taken. In one embodiment, the impression 9 is taken with a tray having an impression material therein. As seen in FIG. 5D, the impression 9 will include the adjacent teeth, the PPCT 1, and the connection between the PPCT 1 and the adjacent teeth, formed by malleable material 8. If required, the impression material is allowed to harden. The adjacent teeth are primed for a bridge. The impression 9 is filled with resin, placed over the primed teeth 6 and the gap, and the resin is allowed to harden. The impression 9 is lifted, and any excess resin is removed. The bridge is then cemented into place. In other embodiments two or more PPCTs 1 and/or APTCs 2 are used.

The linear member 4 can comprise a metal, a textile, a composite, a plastic, or any combination thereof. Additionally the linear member 4 can also be coated; uncoated; round; flat; braided; porous; impermeable; have openings to provide space for the resin and/or the adhesive to reside therein; and combinations thereof. In some embodiments, the linear member 4 is flat and has a width that is substantially equal to the width of the slits 12 it is engaging. This will help maintain alignment of the preforms when making a unit 7, the bridge, or securing the crown. Linear members 4 of different widths can be assigned different colors. One or more linear members 4 can be used and extend over one or more different surfaces.

It is also understood that while the methods have been described using PPTCs and APTCs 1, 2, any combination of PTCs can be used, including PTCs that mimic bicuspids and canines It is also understood that in other embodiments the windows 11 have shapes other than the generally rectangular and triangular shapes shown. It is hereby disclosed that any of methods disclosed may be used with the PPTCs 1 and the APTCs 2.

Depending on the embodiment, certain of the steps of methods described may be removed, others may be added, and the sequence of steps may be altered. Those skilled in the art will now see that certain modifications can be made to the apparatus and methods herein disclosed with respect to the illustrated embodiments, without departing from the spirit of the instant invention. And while the invention has been described above with respect to several embodiments, any element and/or step described in reference to any particular embodiment is hereby disclosed to be associated with any other embodiment of the invention. It is understood that the invention is adapted to numerous rearrangements, modifications, and alterations, and all such arrangements, modifications, and alterations are intended to be within the scope of the invention.

What is claimed is:
1. A method of making dental structures comprising:
providing a malleable material and a preform, the preform comprising a cavity, a mesial window, and a distal window;
inserting the malleable material in the cavity such that the malleable material extrude through the mesial window and the distal window;

placing the preform in a gap between two abutment teeth such that the malleable material is in contact with the two abutment teeth;

taking an impression of the two abutment teeth, the preform, and the malleable material extruding from the preform to the two abutment teeth;

removing the preform and the malleable material;

priming the two abutment teeth to achieve two primed abutment teeth; and filling the impression with a material and applying the impression with the material therein on the two primed abutment teeth.

2. The method of claim 1, wherein the material comprises an acrylic resin.

3. The method of claim 2, wherein the acrylic resin comprises a substance selected from the group consisting of methyl methacrylate, ethyl methacrylate, methyl methacrylate ethyl methacrylate, and bis-acryl.

4. The method of claim 1, wherein the malleable material comprises a substance selected from the group consisting of wax, poly-vinyl siloxane, silicone impression material, silicone putty, alginate, acrylic, or combinations thereof.

5. A method of making dental structures comprising:

providing a malleable material and a preform, the preform comprising: a cavity, a top surface, a lingual surface, a facial surface, a mesial surface, and a distal surface;

a window; wherein the window is defined in the mesial surface, in the distal surface or in each of the mesial surface and the distal surface, and the malleable material is located in the cavity and extrude out of the window;

placing the preform on a gap next to an abutment tooth such that the malleable material is in contact with the abutment tooth;

taking an impression of the abutment tooth, the preform, and the malleable material extruding from the preform to the abutment tooth;

removing the preform and the malleable material;

priming the abutment tooth to achieve a primed abutment tooth; and filling the impression with a material and applying the impression with the material therein on that primed abutment tooth.

* * * * *